United States Patent
Matsuyama et al.

(10) Patent No.: US 8,283,137 B2
(45) Date of Patent: Oct. 9, 2012

(54) PROCESS FOR PRODUCING RECOMBINANT FIBRINOGEN HIGHLY PRODUCING CELL AND HIGHLY PRODUCING CELL

(75) Inventors: Reiko Matsuyama, Kikuchi (JP); Hiroaki Maeda, Kikuchi (JP)

(73) Assignee: Juridical Foundation the Chemo-Sero-Therapeutic Research Institute, Kumamoto (JP)

( * ) Notice: Subject to any disclaimer, the term of this patent is extended or adjusted under 35 U.S.C. 154(b) by 1162 days.

(21) Appl. No.: 10/566,266

(22) PCT Filed: Jul. 28, 2004

(86) PCT No.: PCT/JP2004/010705
§ 371 (c)(1),
(2), (4) Date: May 16, 2008

(87) PCT Pub. No.: WO2005/010178
PCT Pub. Date: Feb. 3, 2005

(65) Prior Publication Data
US 2010/0151522 A1    Jun. 17, 2010

(30) Foreign Application Priority Data

Jul. 29, 2003 (JP) ................................. 2003-282033
Mar. 29, 2004 (JP) ................................. 2004-096215

(51) Int. Cl.
*C12N 1/00* (2006.01)
*C12N 5/10* (2006.01)
*C12N 5/16* (2006.01)
*C12P 21/00* (2006.01)

(52) U.S. Cl. ........................ 435/69.6; 435/69.1; 435/358

(58) Field of Classification Search .................... None
See application file for complete search history.

(56) References Cited

U.S. PATENT DOCUMENTS

| 6,037,457 | A | * | 3/2000 | Lord ............................. 530/413 |
| 6,083,902 | A | | 7/2000 | Cederhom-Williams |
| 7,423,135 | B2 | * | 9/2008 | Estes et al. .................... 536/23.1 |

FOREIGN PATENT DOCUMENTS

| WO | WO9522249 A1 | 8/1995 |
| WO | WO9607728 A1 | 3/1996 |

OTHER PUBLICATIONS

Roy, S.N., et al. 1991 JBC 266(8): 4758-4763.*
Lord et al. 1993 Blood Coagulation and Fibrinolysis 4(1): 55. (abstract only). (1 page total).*
Roy, S., et al. 1994 The Journal of Biological Chemistry 269(1): 691-695.*
Farrell et al., Recombinant human fibrinogen and sulfation of the γ chain, Biochemistry, 30:9414-9420 (1991).
Prunkard et al., High-level expression of recombinant human fibrinogen in the milk of transgenic mice, Nature Biotechnology, 14:867-871 (1996).
Huang et al., The role of βγ and αγ complexes in the assembly of human fibrinogen, The Journal of Biological Chemistry, 271:27942-27947 (1996).
Roy et al., Secretion of biologically active recombinantly fibrinogen by yeast, The Journal of Biological Chemistry, 270(40):23761-23767 (1995).
Lin et al., Stable cell lines expressing baculovirus P35: resistance to apoptosis and nutrient stress, and increased glycoprotein secretion, In Vitro Cell. Dev. Biol.—Animal, 37:293-302 (2001).

* cited by examiner

*Primary Examiner* — Marsha Tsay
(74) *Attorney, Agent, or Firm* — Browdy and Neimark, PLLC

(57) ABSTRACT

When genes encoding three kinds of proteins constituting fibrinogen, an α chain (or variant of α chain), a β chain and a γ chain (or variant of γ chain) are incorporated into an animal cell, a constitutional ratio of respective genes is such that a α chain (and/or variant of γ chain) gene is an equal amount to a 1000-fold amount relative to an α chain (and/or variant of α chain) gene and a β chain gene and, further, by using a baculovirus P35 gene, a recombinant fibrinogen highly producing cell is prepared.

16 Claims, 6 Drawing Sheets

SEQUENCE LISTING

<160> NUMBER OF SEQ ID NOS: 16

<210> SEQ ID NO 1
<211> LENGTH: 45
<212> TYPE: DNA
<213> ORGANISM: Homo sapiens

<400> SEQUENCE: 1
ccccaagctt gtcgacgcca ccatgttttc catgaggatc gtctg            45

<210> SEQ ID NO 2
<211> LENGTH: 60
<212> TYPE: DNA
<213> ORGANISM: Homo sapiens

<400> SEQUENCE: 2
ccatcgatgg atccgtcgac ttactagggg gacagggaag gcttccccaa aggagaagtg   60

<210> SEQ ID NO 3
<211> LENGTH: 60
<212> TYPE: DNA
<213> ORGANISM: Homo sapiens

<400> SEQUENCE: 3
ccccaagctt gtcgacgcca ccatgaaaca tctattattg ctactattgt gtgtttttct   60

<210> SEQ ID NO 4
<211> LENGTH: 60
<212> TYPE: DNA
<213> ORGANISM: Homo sapiens

<400> SEQUENCE: 4

```
cggaattctg atcagtcgac ttactattgc tgtgggaaga agggcctgat cttcatactc    60
```

<210> SEQ ID NO 5
<211> LENGTH: 56
<212> TYPE: DNA
<213> ORGANISM: Homo sapiens

<400> SEQUENCE: 5

```
ccccaagctt gtcgacgcca ccatgagttg gtccttgcac ccccggaatt taattc    56
```

<210> SEQ ID NO 6
<211> LENGTH: 51
<212> TYPE: DNA
<213> ORGANISM: Homo sapiens

<400> SEQUENCE: 6

```
cggaattcgg atccgtcgac ttattaaacg tctccagcct gtttggctcc c    51
```

<210> SEQ ID NO 7
<211> LENGTH: 1980
<212> TYPE: DNA
<213> ORGANISM: Homo sapiens

<400> SEQUENCE: 7

```
ccccaagctt gtcgacgcca ccatgttttc catgaggatc gtctgcctgg tcctaagtgt    60
ggtgggcaca gcatggactg cagatagtgg tgaaggtgac tttctagctg aaggaggagg   120
cgtgcgtggc ccaaggggttg tggaaagaca tcaatctgcc tgcaaagatt cagactggcc   180
cttctgctct gatgaagact ggaactacaa atgcccttct ggctgcagga tgaaagggtt   240
gattgatgaa gtcaatcaag atttacaaa cagaataaat aagctcaaaa attcactatt   300
tgaatatcag aagaacaata aggattctca ttcgttgacc actaatataa tggaaatttt   360
gagaggcgat ttttcctcag ccaataaccg tgataatacc tacaaccgag tgtcagagga   420
tctgagaagc agaattgaag tcctgaagcg caaagtcata gaaaaagtac agcatatcca   480
gcttctgcag aaaaatgtta gagctcagtt ggttgatatg aaacgactgg aggtggacat   540
tgatattaag atccgatctt gtcgagggtc atgcagtagg gctttagctc gtgaagtaga   600
tctgaaggac tatgaagatc agcagaagca acttgaacag gtcattgcca agacttact   660
tccctctaga gataggcaac acttaccact gataaaaatg aaaccagttc cagacttggt   720
tcccggaaat tttaagagcc agcttcagaa ggtaccccca gagtggaagg cattaacaga   780
catgccgcag atgagaatgg agttagagag acctggtgga aatgagatta ctcgaggagg   840
ctccaccctct tatggaaccg atcagagac ggaaagcccc aggaacccta gcagtgctgg   900
aagctggaac tctgggagct ctggacctgg aagtactgga accgaaaacc ctgggagctc   960
tgggactgga gggactgcaa cctggaaacc tgggagctct ggacctgaa gtactggaag  1020
ctggaactct gggagctctg gaactggaag tactggaaac caaaaccctg ggagccctag  1080
acctggtagt accggaacct ggaatcctgg cagctctgaa gcggaagtg ctgggcactg  1140
gacctctgag agctctgtat ctggtagtac tggacaatgg cactctgaat ctggaagttt  1200
taggccagat agcccaggct ctgggaacgc gaggcctaac aacccagact ggggcacatt  1260
tgaagaggtg tcaggaaatg taagtccagg acaaggaga gagtaccaca cagaaaaact  1320
ggtcacttct aaaggagata aagagctcag gactggtaaa gagaaggtca cctctggtag  1380
cacaaccacc acgcgtcgtt catgctctaa aaccgttact aagactgtta ttggtcctga  1440
tggtcacaaa gaagttacca aagaagtggt gacctccgaa gatggttctg actgtcccga  1500
```

```
ggcaatggat ttaggcacat tgtctggcat aggtactctg gatgggttcc gccataggca    1560
ccctgatgaa gctgccttct tcgacactgc ctcaactgga aaaacattcc caggtttctt    1620
ctcacctatg ttaggagagt ttgtcagtga gactgagtct aggggctcag aatctggcat    1680
cttcacaaat acaaggaat ccagttctca tcaccctggg atagctgaat tcccttcccg     1740
tggtaaatct tcaagttaca gcaaacaatt tactagtagc acgagttaca acagaggaga    1800
ctccacattt gaaagcaaga gctataaaat ggcagatgag gccggaagtg aagccgatca    1860
tgaaggaaca catagcacca agagaggcca tgctaaatct cgccctgtca gaggtatcca    1920
cacttctcct ttggggaagc cttccctgtc cccctagtaa gtcgacggat ccatcgatgg    1980
```

<210> SEQ ID NO 8
<211> LENGTH: 1479
<212> TYPE: DNA
<213> ORGANISM: Homo sapiens
<400> SEQUENCE: 8

```
ccccaagctt gtcgacgcca ccatgaaaca tctattattg ctactattgt gtgttttct      60 agttaagtcc caaggtgtca acgacaatga ggagggtttc ttcagtgccc gtggtcatcg    120
accccttgac aagaagagag aagaggctcc cagcctgagg cctgccccac cgcccatcag    180
tggaggtggc tatcgggctc gtccagccaa agcagctgcc actcaaaaga agtagaaag     240 aaaagcccct gatgctggag gctgtcttca cgctgaccca gacctggggg tgttgtgtcc    300
tacaggatgt cagttgcaag aggctttgct acaacaggaa aggccaatca gaaatagtgt    360
tgatgagtta ataacaatg tggaagctgt ttcccagacc tcctcttctt cctttcagta    420
catgtatttg ctgaaagacc tgtggcaaaa gaggcagaag caagtaaaag ataatgaaaa    480
tgtagtcaat gagtactcct cagaactgga aaagcaccaa ttatatatag atgagactgt    540
gaatagcaat atcccaacta accttcgtgt gcttcgttca atcctggaaa acctgagaag    600
caaaatacaa aagttagaat ctgatgtctc agctcaaatg gaatattgtc gcaccccatg    660
cactgtcagt tgcaatattc ctgtggtgtc tggcaaagaa tgtgaggaaa ttatcaggaa    720
aggaggtgaa acatctgaaa tgtatctcat tcaacctgac agttctgtca aaccgtatag    780
agtatactgt gacatgaata cagaaaaatgg aggatggaca gtgattcaga accgtcaaga    840
cggtagtgtt gactttggca ggaaatggga tccatataaa cagggatttg gaaatgttgc    900
aaccaacaca gatgggaaga attactgtgg cctaccaggt gaatattggc ttggaaatga    960
taaaattagc cagcttacca ggatgggacc cacagaactt ttgatagaaa tggaggactg   1020
gaaaggagac aaagtaaagg ctcactatgg aggattcact gtacagaatg aagccaacaa   1080
ataccagatc tcagtgaaca aatacagagg aacagccggt aatgccctca tggatggagc   1140
atctcagctg atgggagaaa acaggaccat gaccattcac aacggcatgt tcttcagcac   1200
gtatgacaga gacaatgacg gctggttaac atcagatccc agaaaacagt gttctaaaga   1260
agacggtggt ggatggtggt ataatagatg tcatgcagcc aatccaaacg gcagatacta   1320 ctgggggtgga cagtacacct gggacatggc aaagcatggc acagatgatg gtgtagtatg   1380
gatgaattgg aagggtcat ggtactcaat gaggaagatg agtatgaaga tcaggccctt    1440
cttcccacag caatagtaag tcgactgatc agaattccg                            1479
```

<210> SEQ ID NO 9
<211> LENGTH: 1359
<212> TYPE: DNA
<213> ORGANISM: Homo sapiens

<400> SEQUENCE: 9

```
ccccaagctt gtcgacgcca ccatgagttg gtccttgcac ccccggaatt taattctcta      60
cttctatgct cttttatttc tctcttcaac atgtgtagca tatgttgcta ccagagacaa     120
ctgctgcatc ttagatgaaa gattcggtag ttattgtcca actacctgtg gcattgcaga    180
tttcctgtct actatcaaa ccaaagtaga caaggatcta cagtctttgg aagacatctt     240
acatcaagtt gaaacaaaa catcagaagt caaacagctg ataaaagcaa tccaactcac     300
ttataatcct gatgaatcat caaaaccaaa tatgatagac gctgctactt tgaagtccag    360
gaaaatgtta gaagaaatta tgaaatatga agcatcgatt ttaacacatg actcaagtat   420
tcgatatttg caggaaatat ataattcaaa taatcaaaag attgttaacc tgaaagagaa   480
ggtagcccag cttgaagcac agtgccagga accttgcaaa gacacggtgc aaatccatga   540
tatcactggg aaagattgtc aagacattgc caataaggga gctaaacaga gcgggctttta  600
ctttattaaa cctctgaaag ctaaccagca attcttagtc tactgtgaaa tcgatgggtc   660
tggaaatgga tggactgtgt ttcagaagag acttgatggc agtgtagatt tcaagaaaaa   720
ctggattcaa tataagaag gatttggaca tctgtctcct actggcacaa cagaatttttg   780
gctgggaaat gagaagattc atttgataag cacacagtct gccatcccat atgcattaag   840
agtggaactg gaagactgga atggcagaac cagtactgca gactatgcca tgttcaaggt   900
gggacctgaa gctgacaagt accgcctaac atatgcctac ttcgctggtg gggatgctgg   960
agatgccttt gatggctttg attttggcga tgatcctagt gacaagtttt tcacatccca  1020
taatggcatg cagttcagta cctgggacaa tgacaatgat aagtttgaag gcaactgtgc  1080
tgaacaggat ggatctggtt ggtggatgaa caagtgtcac gctggccatc tcaatggagt  1140
ttattaccaa ggtggcactt actcaaaagc atctactcct aatggttatg ataatggcat  1200
tatttgggcc acttggaaaa cccggtggta ttccatgaag aaaaccacta tgaagataat  1260
cccattcaac agactcacaa ttggagaagg acagcaacac cacctggggg gagccaaaca  1320
ggctggagac gtttaataag tcgacggatc cgaattccg                          1359
```

<210> SEQ ID NO 10
<211> LENGTH: 60
<212> TYPE: DNA
<213> ORGANISM: Baculovirus

<400> SEQUENCE: 10

```
ccgctcgagg aattcgccac catgtgtgta atttttccgg tagaaatcga cgtgtcccag     60
```

<210> SEQ ID NO 11
<211> LENGTH: 54
<212> TYPE: DNA
<213> ORGANISM: Baculovirus

<400> SEQUENCE: 11

```
ccgctcgagg aattctactc gtaaagccag ttcaatttta aaaacaaatg acat           54
```

<210> SEQ ID NO 12
<211> LENGTH: 1035
<212> TYPE: DNA
<213> ORGANISM: Baculovirus

<400> SEQUENCE: 12

```
ccgctcgagg aattcgccac catgtgtgta atttttccgg tagaaatcga cgtgtcccag     60
acgattattc gagattgtca ggtggacaaa caaaccagag agttggtgta cattaacaag    120
```

```
attatgaaca cgcaattgac aaaacccgtt ctcatgatgt ttaacatttc gggtcctata    180
cgaagcgtta cgcgcaagaa caacaatttg cgcgacagaa taaaatcaaa agtcgatgaa    240
caatttgatc aactagaacg cgattacagc gatcaaatgg atggattcca cgatagcatc    300
aagtatttta aagatgaaca ctattcggta agttgccaaa atggcagcgt gttgaaaagc    360
aagtttgcta aaattttaaa gagtcatgat tataccgata aaaagtctat tgaagcttac    420
gagaaatact gtttgcccaa attggtcgac gaacgcaacg actactacgt ggcggtatgc    480
gtgttgaagc cgggatttga gaacggcagc aaccaagtgc tatctttcga gtacaacccg    540
attggtaaca aagttattgt gccgtttgct cacgaaatta acgacacggg actttacgag    600
tacgacgtcg tagcttacgt ggacagtgtg cagtttgatg cgaacaatt tgaagagttt    660 gtgcagagtt taatattgcc gtcgtcgttc aaaaattcgg aaaaggtttt atattacaac    720
gaagcgtcga aaacaaaag catgatctac aaggctttag agtttactac agaatcgagc    780
tggggcaaat ccgaaaagta taattggaaa attttttgta acggttttat ttatgataaa    840
aaatcaaaag tgttgtatgt taaattgcac aatgtaacta gtgcactcaa caaaaatgta    900
atattaaaca caattaaata aatgttaaaa tttattgcct aatattattt tgtcattgct    960
tgtcatttat taatttggat gatgtcattt gttttttaaaa ttgaactggc tttacgagta   1020
gaattcctcg agcgg                                                     1035

<210> SEQ ID NO 13
<211> LENGTH: 77
<212> TYPE: DNA
<213> ORGANISM: Homo sapiens

<400> SEQUENCE: 13
ccatcgatgg atccgtcgac ttactattgg gtcacaaggg gcctaatttt catgcgaaca    60
gccctgaggg aatatag                                                   77

<210> SEQ ID NO 14
<211> LENGTH: 2646
<212> TYPE: DNA
<213> ORGANISM: Homo sapiens

<400> SEQUENCE: 14
ccccaagctt gtcgacgcca ccatgttttc catgaggatc gtctgcctgg tcctaagtgt    60
ggtgggcaca gcatggactg cagatagtgg tgaaggtgac tttctagctg aaggaggagg   120
cgtgcgtggc ccaagggttg tggaaagaca tcaatctgcc tgcaaagatt cagactggcc   180
cttctgctct gatgaagact ggaactacaa atgcccttct ggctgcagga tgaaagggtt   240
gattgatgaa gtcaatcaag attttacaaa cagaataaat aagctcaaaa attcactatt   300
tgaatatcag aagaacaata aggattctca ttcgttgacc actaatataa tggaaatttt   360
gagaggcgat ttttcctcag ccaataaccg tgataatacc tacaaccgag tgtcagagga   420
tctgagaagc agaattgaag tcctgaagcg caaagtcata gaaaagtac agcatatcca   480 gcttctgcag aaaaatgtta gagctcagtt ggttgatatg aaacgactgg aggtggacat   540
tgatattaag atccgatctt gtcgagggtc atgcagtagg ctttagctc gtgaagtaga   600 tctgaaggac tatgaagatc agcagaagca acttgaacag gtcattgcca aagacttact   660 tcccctctaga gataggcaac acttaccact gataaaaatg aaaccagttc cagacttggt   720 tccccggaaat tttaagagcc agcttcagaa ggtaccccca gagtggaagg cattaacaga   780
catgccgcag atgagaatgg agttagagag acctggtgga aatgagatta ctcgaggagg   840
```

```
ctccacctct tatggaaccg gatcagagac ggaaagcccc aggaacccta gcagtgctgg      900
aagctggaac tctgggagct ctggacctgg aagtactgga aaccgaaacc ctgggagctc      960
tgggactgga gggactgcaa cctggaaacc tgggagctct ggacctggaa gtactggaag     1020
ctggaactct gggagctctg aactggaag tactggaaac caaaaccctg ggagccctag      1080
acctggtagt accggaacct ggaatcctgg cagctctgaa cgcggaagtg ctgggcactg     1140
gacctctgag agctctgtat ctggtagtac tggacaatgg cactctgaat ctggaagttt     1200
taggccagat agcccaggct ctgggaacgc gaggcctaac aacccagact ggggcacatt     1260
tgaagaggtg tcaggaaatg taagtccagg acaaggaga gagtaccaca cagaaaaact      1320
ggtcacttct aaaggagata aagagctcag gactggtaaa gagaaggtca cctctggtag     1380
cacaaccacc acgcgtcgtt catgctctaa aaccgttact aagactgtta ttggtcctga     1440
tggtcacaaa gaagttacca agaagtggt gacctccgaa gatggttctg actgtcccga     1500
ggcaatggat ttaggcacat tgtctggcat aggtactctg gatgggttcc gccataggca     1560
ccctgatgaa gctgccttct tcgacactgc ctcaactgga aaaacattcc caggtttctt     1620
ctcacctatg ttaggagagt ttgtcagtga gactgagtct aggggctcag aatctggcat     1680
cttcacaaat acaaaggaat ccagttctca tcaccctggg atagctgaat tcccttcccg     1740
tggtaaatct tcaagttaca gcaaacaatt tactagtagc acgagttaca acagaggaga     1800
ctccacattt gaaagcaaga gctataaaat ggcagatgag gccggaagtg aagccgatca     1860
tgaaggaaca catagcacca agagaggcca tgctaaatct cgccctgtca gagactgtga     1920
tgatgtcctc caaacacatc cttcaggtac ccaaagtggc atttttcaata tcaagctacc     1980 gggatccagt aagattttt ctgtttattg cgatcaagag accagtttgg gaggatggct      2040
tttgatccag caaagaatgg atggatcact gaattttaac cggacctggc aagactacaa     2100
gagaggtttc ggcagcctga tgacgaggg ggaaggagaa ttctggctag caatgactca      2160
cctccactta ctaacccaaa ggggctctgt tcttagggtt gaattagagg actgggctgg     2220
gaatgaagct tatgcagaat atcacttccg ggtaggctct gaggctgaag gctatgccct     2280
ccaagtctcc tcctatgaag gcactgcggg tgatgctctg attgagggtt ccgtagagga     2340
aggggcagag tacacctctc acaacaacat gcagttcagc acctttgaca gggatgcaga     2400
ccagtgggaa gagaactgtg cagaagtcta tgggggaggc tggtggtata taactgcca      2460 agcagccaat ctcaatggaa tctactaccc tgggggctcc tatgacccaa ggaataacag     2520
tccttatgag attgagaatg gagtggtctg ggtttccttt agaggggcag attattccct     2580
cagggctgtt cgcatgaaaa ttaggcccct tgtgacccaa tagtaagtcg acggatccat     2640
cgatgg                                                                2646
```

<210> SEQ ID NO 15
<211> LENGTH: 77
<212> TYPE: DNA
<213> ORGANISM: Homo sapiens

<400> SEQUENCE: 15

```
cggaattcgg atccgtcgac ttactacaaa tcatcctcag ggtaaagtga gtcatattct       60
gtttccgcag ggtgctc                                                      77
```

<210> SEQ ID NO 16
<211> LENGTH: 1407
<212> TYPE: DNA
<213> ORGANISM: Homo sapiens

```
<400> SEQUENCE: 16
ccccaagctt gtcgacgcca ccatgagttg gtccttgcac ccccggaatt taattctcta    60
cttctatgct cttttatttc tctcttcaac atgtgtagca tatgttgcta ccagagacaa   120
ctgctgcatc ttagatgaaa gattcggtag ttattgtcca actacctgtg gcattgcaga   180
tttcctgtct acttatcaaa ccaaagtaga caaggatcta cagtctttgg aagacatctt   240
acatcaagtt gaaaacaaaa catcagaagt caaacagctg ataaaagcaa tccaactcac   300
ttataatcct gatgaatcat caaaaccaaa tatgatagac gctgctactt tgaagtccag   360
gaaaatgtta gaagaaatta tgaaatatga agcatcgatt ttaacacatg actcaagtat   420
tcgatatttg caggaaatat ataattcaaa taatcaaaag attgttaacc tgaaagagaa   480
ggtagcccag cttgaagcac agtgccagga accttgcaaa gacacggtgc aaatccatga   540
tatcactggg aaagattgtc aagacattgc caataaggga gctaaacaga gcgggcttta   600
ctttattaaa cctctgaaag ctaaccagca attcttagtc tactgtgaaa tcgatgggtc   660
tggaaatgga tggactgtgt ttcagaagag acttgatggc agtgtagatt tcaagaaaaa   720
ctggattcaa tataaagaag gatttggaca tctgtctcct actggcacaa cagaattttg   780
gctgggaaat gagaagattc atttgataag cacacagtct gccatcccat atgcattaag   840
agtggaactg gaagactgga atggcagaac cagtactgca gactatgcca tgttcaaggt   900
gggacctgaa gctgacaagt accgcctaac atatgcctac ttcgctggtg gggatgctgg   960
agatgccttt gatggctttg attttggcga tgatcctagt gacaagtttt tcacatccca  1020
taatggcatg cagttcagta cctgggacaa tgacaatgat aagtttgaag gcaactgtgc  1080
tgaacaggat ggatctggtt ggtggatgaa caagtgtcac gctggccatc tcaatggagt  1140
ttattaccaa ggtggcactt actcaaaagc atctactcct aatggttatg ataatggcat  1200
tatttgggcc acttggaaaa cccggtggta ttccatgaag aaaaccacta tgaagataat  1260
cccattcaac agactcacaa ttggagaagg acagcaacac cacctggggg gagccaaaca  1320
ggtcagacca gagcaccctg cggaaacaga atatgactca ctttaccctg aggatgattt  1380
gtagtaagtc gacggatccg aattccg                                      1407
```

PROCESS FOR PRODUCING RECOMBINANT FIBRINOGEN HIGHLY PRODUCING CELL AND HIGHLY PRODUCING CELL

BACKGROUND OF THE INVENTION

1. Field of the Invention

The present invention relates to a process for producing a recombinant fibrinogen producing cell producing a large amount of fibrinogen which is one of plasma proteins. More particularly, the present invention relates to a process for producing a recombinant fibrinogen producing cell comprising a step of incorporating, into an animal cell, genes encoding three kinds of proteins constituting fibrinogen, an α chain (or variant of α chain), a β chain and a γ chain (or variant of γ chain) at a constitutional ratio thereof so that the number of a γ chain (and/or variant of γ chain) gene is an equivalent amount to a 1000-fold amount relative to a total number of an α chain (and/or variant of α chain) gene and a β chain gene, and a step of incorporating a production amount enhancing factor, and a recombinant fibrinogen highly producing cell obtained by the process, and fibrinogen obtained therefrom.

2. Description of the Related Art

Fibrinogen is responsible for serving to coagulate a blood when a living body undergoes injury, as one of blood coagulation factors. The first function is to form a body of a thrombus called fibrin clot at a site of injury, and the second function is to serve as an adhesive protein necessary for platelet aggregation. A blood concentration of fibrinogen is usually about 3 mg/ml, and is third highest next to albumin, and immunoglobulin G.

Fibrinogen is a macro-glycoprotein consisting of a total 6 of polypeptides having each two of three kinds of different polypeptides called α chain, β chain and γ chain. An individual molecular weight of polypeptides is about 67000 in the case of an α chain, about 56000 in the case of a β chain, and about 47500 in the case of a γ chain, and a molecular weight of fibrinogen as an aggregate of them reaches about 340000 (see "Hemostasis•Thrombus•Fibrinolysis", Matsuda and Suzuki ed., Chugaiiyakusha (1994)). In a fibrinogen molecule, a half molecules of an α chain, a β chain and a α chain which are S—S bonded (α-β-γ) form a further S—S bonded dimer (α-β-γ)$_2$, and the fibrinogen molecule has a shape of three nodular (knotting spherical) structures. That is, the fibrinogen molecule takes a structure consisting of a central E region, two D regions symmetrically disposed on both outer sides thereof, and a rod-like part connecting therebetween.

In fibrinogen in blood, heterogenous molecules due to possession of variant polypeptides having different molecular sizes are present. For example, in a γ chain, the presence of a variant called γ' chain (or γB chain) is reported, and this has been revealed to be a polypeptide comprising a total 427 of amino acid residues in which 20 amino acid residues are added to a 408-position of an amino acid sequence of a γ chain (see Chung D E and Davie E W, Biochemistry, 23, 4232 (1984)). In addition, in an α chain, a variant called αE is present, and it is reported that this polypeptide has a total 847 of amino acid residues in which 236 amino acids are extended at a 612-position of an amino acid sequence of an α chain (see Lawrence Y F et al., Biochemistry, 31, 11968 (1992)). A remarkable difference in its aggregating ability and the fibrinolysis resistance ability is not recognized in heterogenous fibrinogen having γ' and αE as compared with normal fibrinogen. However, these molecular species are under study, and the detailed function has not been elucidated yet.

A fibrinogen preparation is effective in arresting serious bleeding by enhancing a fibrinogen concentration in blood by a method such as intravenous administration, and is used in improving the consumption state of a blood coagulation factor such as disseminated intravascular coagulation (DIC) in sepsis, or supplemental therapy in congenital or acquired fibrinogen deficiency. In addition, a fibrinogen preparation is widely utilized as a tissue adhesive utilizing agglutination property of fibrin (see "Special Edition•Bioadhesive" Biomedical Perspectives, 6, 9-72 (1997)). This living body-derived adhesive utilizes gelling of fibrinogen in a living body, and is widely used in hemostasis, closure of a wound site, adhesion or suturing reinforcement of nerve, tendon, vessel and tissue, and closure of air leakage in lung. In addition, in recent years, a preparation which has enhanced convenience by adhering fibrinogen to a sheet of collagen has been sold.

Currently, fibrinogen used as a medicament is prepared from human plasma, and a problem has been exemplified that 1) since plasma collected from unspecific many humans is used, there is a crisis that infective pathogen such as a virus causing pneumonia such as HAV, HBV, HCV, HEV and TTV, a virus causing immunodeficiency such as HIV, and abnormal prion causing CJD is mixed in, and 2) in Japan, plasma is supplied by blood donation, and future stable supply is problematic.

In order to solve these problems, recombination of fibrinogen has been previously tried. For example, in *Escherichia coli*, expression of a fibrinogen γ chain in a bacterial cell has been succeeded, but there is no report that three proteins of an a chain, a β chain and a γ chain are simultaneously expressed to produce a functional fibrinogen molecule. In addition, also in an expression system using yeast, there was transiently a report that secretion and expression have been successful, but finally reproductivity was not confirmed, and the report was canceled (see Redman C M, Kudryk B., J. Biol. Chem., 274, 554 (1999)). Like this, there has been not a report yet that fibrinogen has been successfully expressed using *Escherichia coli* or yeast.

On the other hand, in an animal cell, expression has been tried using a BHK cell (see Farrell D H et al., Biochemistry, 30, 9414 (1991)), a COS cell (see Roy S N et al., J. Biol. Chem., 266, 4758 (1991)) or a CHO cell (see Lord S T et al., Blood Coagul Fibrinolysis, 4, 55 (1993), Binnie C G et al., Biochemistry, 32, 107 (1993) and Lord S T et al., Biochemistry, 35, 35, 2342 (1996), and U.S. Pat. No. 6,037,457), but the production amount is only around 1 to 15 μg/ml. In these cases, using any of a metallothionein promoter, a Rous sarcoma virus LTR promoter, and an adenovirus 2 major late promoter, and any of an aminoglycoside 3' phosphotransferase (neo) gene, a dihydrofolate reductase (dhfr) gene, and a histidinol resistance gene or a combination thereof is used as a selectable marker. In any case, a method of independently constructing expression vectors for genes encoding an α chain, a β chain and a γ chain, respectively, and transfecting a cell with three vectors simultaneously, or introducing an expression vector having a β chain gene and an α chain gene later into a cell which has been previously transformed with two expression vectors, each having an α chain gene and aβ chain gene, or a β chain gene and a γ chain gene, and a method of mixing a plasmid having an α chain gene and a β chain gene and a plasmid having a β chain gene at an equal amount, and introducing the mixture is adopted. In any case, there is, particularly, no description regarding a constitutional ratio of respective genes upon introduction, and it is thought that respective genes are equally introduced according to a general procedure. In a medicament using fibrinogen derived from blood which is currently used, for example, in a fibrin paste preparation, about 80 mg/dose of fibrinogen is used and, at an expression amount of the aforementioned more than a dozen μg/ml, a production facility must be scaled up, necessarily leading to the high cost. In order to produce fibrinogen at a practical level by the gene recombinant technique, a highly producing cell (e.g. expression amount of fibrinogen is 100 μg/ml or more) is necessary, but currently, there is no report of an expression system using a recombinant animal cell satisfying this.

On the other hand, when a recombinant fibrinogen producing cell is cultured, the same problem as that of culturing of a normal animal cell is contemplated. In general, when a protein is a secreted protein, since an objective protein can be recovered in the culture supernatant, a method of culturing a recombinant animal cell in a suitable medium, culturing it for a certain term and, thereafter, recovering the culture supernatant at once (batch culturing), or extracting a suitable amount of a medium at an arbitral time, and performing addition continuously (perfusion culturing) is used. In any event, as the number of a recombinant animal cell producing an objective secreted protein is increased, an amount of a secreted protein accumulated (produced) in a medium is increased. Growth of a cell is divided into three phases: a logarithmic phase when a cell is grown logarithmically, a stationary phase when the number of cells is apparently constant, and a death phase when a cell dies, and the number of cells is decreased. In order to increase production of a secreted protein, it is important to enhance a cell density of a recombinant animal cell at a stationary phase as high as possible, and maintain the term as long as possible. Particularly, in the case of batch culturing, since a recombinant animal cell is grown in a constant amount of a medium, many attempts have been tried to enhance a cell density at a stationary phase as high as possible in order to increase a production amount of a secreted protein therein, and maintain the term as long as possible.

As a method different from such the rearing method, an attempt has been also tried to modify a host cell. For example, a method using an anti-apoptotic factor has been tried. This method tries to express an anti-apoptotic factor gene in a recombinant animal cell producing a protein, and imparting the ability of suppressing programmed cell death (apoptosis) generated by nutrient starving to the cell to extent a stationary phase.

A mechanism causing apoptosis is thought as follows according to "Apoptosis and Disease Central Nervous System Disease" Yoshikuni Mizuno ed., Drug Journal (2000). When a variety of cell death stimulations such as nutrient depletion is transmitted to a cell, the signal is transmitted to mitochondria via various proteins including a transcription factor and a kinase. Mitochondria which has received the signal releases an apoptosis signal transmitting factor (AIF, cytochrome c etc.) into a cytoplasm. Cytochrome c together with Apaf-1 (apoptosis activating factor-1) present in a cytoplasm is bound to pro-caspase-9 to form a complex, activating caspase-9. An activated caspase cascade cuts various substrates in a cytoplasm or a nucleus, and induces a morphological or a biochemical change (actin degradation, DNA fragmentation, chromosome aggregation etc.) characteristic in various apoptoses. As a factor which suppresses such the apoptosis, Bcl-2 (B cell lymphoma/leukemia 2) is well-known. A Bcl-2 gene was found as an oncogene which is frequently seen in human follicular lymphoma. Currently, many family genes having a domain (BH1-4) having high homology with Bcl-2 have been identified. In a family, there are factors which suppressively serve in apoptosis, and factors which promotively serve and, as an suppressible factor, for example, Bcl-xL, Bcl-w, Mcl-1, A1, BHRF1, E1B-19K, and Ced-9 are known, and it is though that the factor arrests signal transmission by inhibiting the aforementioned release of cytochrome c or binding with Apaf-1 and procaspase-9. It is thought that such the suppressible Bcl-2 family functions upstream of a caspase cascade.

On the other hand, a factor which acts downstream of a caspase cascade (inhibits activity of caspase directly) to show anti-apoptotic effect is also known. For example, a P35 protein of AcNPV (Autogropha californica nuclear polyhedrosis virus) belonging to a Baculovirus family is cut as a substrate of caspase, a fragment thereof forms a stable composite with almost all caspases to inhibit its activity. Therefore, various apoptosis can be suppressed. BmNPV (*Bombyx mori* nuclear polyhedrosis virus) which is close to AcNPV also has a P35 gene. In addition, crmA of cowpox virus specifically binds to caspase-1-like protease and caspase-8, -10, and inhibits this, thereby, apoptosis can be suppressed. In addition, v-FLIP derived from herpesvirus has two DEDs (death effector domains), and suppresses activation of caspase-8 by binding to FADD (Fas-associating Protein with death domain).

Further, in many close viruses including CpGV (Cidia pomonella granulosis virus) and OpMNPV (Orgyia pseudotsugata multinucleocapsid nucleopolyhedrovirus) of Baculovirus family, a v-IAP (inhibitor of apoptosis) gene whose expression product inhibits directly caspase activity has been identified besides a P35 gene. Up to now, as a homologue of v-IPA, an IPA family having a few kinds of BIRs (baculovirus IPA repeats) such as c-IAP1/hia-2, c-IAP2/hia-1, XIAP, NAIP, survivin, TIAP, Apollon, DIAP1, DIAP2, SfIAP, and ITA has been identified in a *drosophila* and a mammal in addition to a virus.

However, methods of potentiating a production amount using an anti-apoptotic factor derived from a Bcl-2 family such as Bcl-2, Bcl-xL, and E1B-19K which acts on upstream of a cascade are all inhibit cell death, and can extend a stationary phase of a growth carve, but a production amount is not increased as expected, in many cases. From these things, it is thought that these factors have no direct effect of potentiating production amount of a protein, or if present, exerts the effect under the special environment. On the other hand, regarding a caspase inhibiting action factor which acts on downstream of a cascade, there is few reports in which a relationship with the production amount potentiating effect was investigated in a recombinant protein producing cell, and the effect has been unknown.

SUMMARY OF THE INVENTION

As described above, in production and selling of a fibrinogen preparation derived from blood, mixing of an infective pathogen and stable supply to a market must be feared. In order to solve these problems, production of fibrinogen by the gene recombinant technique has been tried, but at an expression amount which has previously been reported, it is predicted that it is difficult to put into practice from a viewpoint of the production cost, and improvement is demanded. Further, many is unknown about the action of a stationary phase extending factor which has previously been used in potentiating a production amount, and the detailed study has been sought.

Therefore, an object of the present invention is to provide a process for producing a recombinant human fibrinogen highly producing cell which highly expresses human fibrinogen.

In addition, another object of the present invention is to elucidate influence of the production amount potentiating action due to baculovirus P35 upon production of a recombinant fibrinogen highly producing cell, and provide a method of further potentiating a production amount of fibrinogen.

Further, another object of the present invention is to provide a recombinant human fibrinogen highly producing cell obtained by the method, and fibrinogen.

In order to attain the aforementioned objects, the present inventors continued to study intensively and, as a result, found out that a recombinant animal cell which easily expresses human fibrinogen highly can be produced by mixing, for example, an expression vector in which a gene encoding an α chain and a γ chain has been incorporated, and an expression vector in which a gene encoding a β chain and a γ chain has been incorporated at an equal amount, so that the number of a γ chain (and/or variant of γ chain) gene is an equal amount to a 1000-fold amount relative to a total number of an α chain (and/or variant of α chain) gene and a β chain gene, among three kinds of proteins constituting human fibrinogen, and transforming an animal cell using this, which resulted in completion of the present invention.

Therefore, the present invention encompasses a process for producing a recombinant human fibrinogen highly producing cell, comprising a step of transforming an animal cell using an expression vector obtained by mixing an α chain and γ chain-containing expression vector and a β chain and γ chain-containing expression vector at an equal amount.

Further, in order to attain production amount potentiation from another angle, the present inventors continued to study intensively and, as a result, found out that a production amount is further potentiated by transforming an animal cell using a baculovirus P35 gene. Further, the present inventors made clear that this potentiation of a production amount contemplates two ways of the case where this factor contributes to potentiation of protein biosynthesis activity as a production amount potentiating factor, and the case where the factor contributes to inhibition of apoptosis activity and, in the case of the former, it was found out that since potentiation of a production amount is obtained before one does not wait for timing of occurrence of apoptosis, a medium is not selective, and an industrial utilization value is very high.

Therefore, the present invention encompasses a process for producing a recombinant fibrinogen highly producing cell which can further potentiate a production amount by transforming a fibrinogen producing cell using a baculovirus P35 gene simultaneously or at different time.

In addition, the present invention encompasses a recombinant human fibrinogen highly producing cell which highly expresses human fibrinogen, and fibrinogen obtained by the above process.

According to the method of mixing-expressing genes encoding three kinds of proteins constituting human fibrinogen, a recombinant producing cell which highly expresses fibrinogen, and a process for producing the same are provided. As a result, a production amount of about 100 to 1520 μg/ml is obtained. An amount of fibrinogen produced by the recombinant human fibrinogen producing cell of the present invention considerably exceeds an amount of expression of fibrinogen (~15 μg/ml) by the previously reported gene recombination technique. Further, when transformation with the production amount potentiating factor gene of the present invention is performed, a production amount which far exceeds a production amount by the previous art, such as 704 to 3952 μg/ml is obtained, and it becomes possible to supply a large amount to a market from now on. Further, since a method of culturing the same is not limited, and a production amount can be increased before advent of apoptosis, a large amount of a production amount can be obtained in a short term. Therefore, the recombinant human fibrinogen producing cell of the present invention enables to establish a process for producing human fibrinogen at a practical level and, by establishment of the process, stable supply of human fibrinogen to a market is maintained.

In addition, when a recombinant human fibrinogen producing cell obtained by the present process is used, mixing of an infective pathogen which is feared when prepared using blood as the previous raw material, and involvement of other blood-derived components can be excluded, and it becomes possible to produce and supply a more safe human fibrinogen preparation effectively and at a large amount. Like this, the process of the present invention can be also utilized as a process for producing a recombinant fibrinogen producing cell which highly produces fibrinogen other than fibrinogen derived from human plasma.

DESCRIPTION OF THE PREFERRED EXAMPLES

Figure 1:
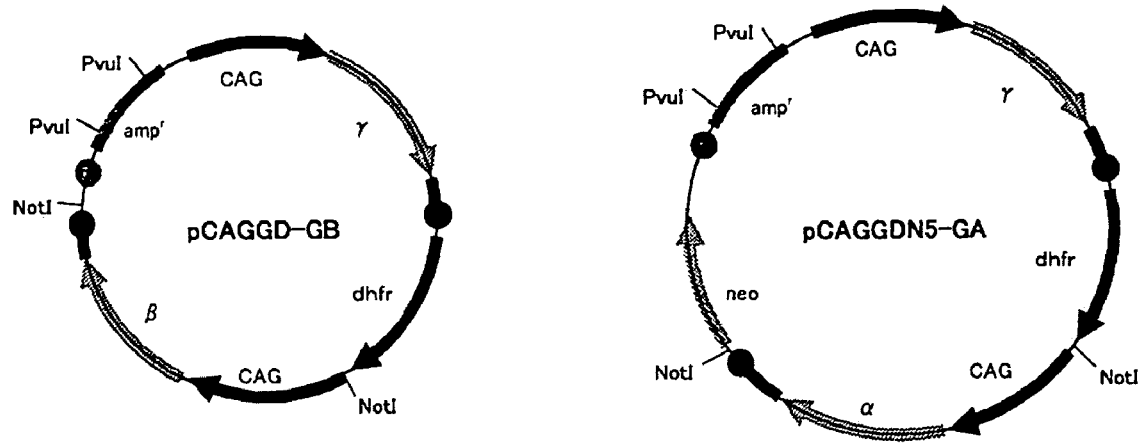
FIG. 1 is a view showing an expression vector for producing a recombinant fibrinogen producing cell.

The process of the present invention is characterized by a process for producing a recombinant fibrinogen producing cell, comprising a step of incorporating genes encoding three kinds of proteins constituting fibrinogen, an α chain, a β chain and a γ chain into an animal cell, at a constitutional ratio of respective genes, so that the number of a γ chain (and/or variant of γ chain) is an equal amount to a 1000-fold amount relative to a total number of an α chain (and/or variant of α chain) gene and a β chain gene. Further, the process is characterized by transforming with a baculovirus P35 gene which is a production amount potentiating factor.

In the present invention, mainly, human fibrinogen is handled, but the present invention can be also used as a process for producing a fibrinogen producing cell of other animal without limiting to human. As genes encoding constitutional polypeptides, an α chain, a β chain and a γ chain of human fibrinogen used in the present invention, any of a cDNA gene and a chromosome gene can be used as far as it is a gene by which the expression product can be finally assembled to form a human fibrinogen molecule.

As described above, variants called an αE chain and a γ' (γB) chain, respectively, are present in an α chain and a γ chain. In addition to them, a gene encoding other variant polypeptide which may be newly found out from now on can be used in the present invention as far as its expression product functions as a protein constituting a fibrinogen molecule.

A desired gene can be obtained, for example, by designing PCR primers based on sequences reported in the literature (see Rixon M W et al., Biochemistry, 22, 3237 (1983), Chung D W et al., Biochemistry, 22, 3244 (1983), Chung D W et al., Biochemistry, 22, 3250 (1983), Chung D E and Davie E W, Biochemistry, 23, 4232 (1984) and Lawrence Y F et al., Biochemistry, 31, 11968 (1992)), respectively, and performing PCR using a cDNA derived from an organ or a cell producing fibrinogen such as human liver as a template.

More specifically, cDNAs encoding an α chain, a β chain, a γ chain, an αE chain and a γ' chain of fibrinogen are prepared as follows: First, a total RNA is extracted from a human hepatocyte, and a mRNA is purified from this. The resulting mRNA is converted into a cDNA, a PCR reaction is performed using PCR primers designed in conformity with respective gene sequences, and the resulting PCR product is incorporated into a plasmid vector, and is introduced into *Escherichia coli*. A clone having a cDNA encoding an objective protein is selected from *Escherichia coli* colonies. For extracting the above total RNA, a reagent such as a commercially available TRIzol reagent (GIBCO BRL), ISOGEN (Nippon Gene Co., Ltd.) and the like is used and, for purifying a mRNA, a commercially available kit such as mRNA Purification Kit (Amersham BioSciences) is used and, for conversion into a cDNA, a commercially available kit for preparing a cDNA library such as SuperScript plasmid system for cDNA synthesis and plasmid cloning (GIBCO BRL) is used, respectively. When a human fibrinogen gene is obtained, a commercially available cDNA library such as Human Liver Marathon-Ready cDNA (BD Bioscience) is used. PCR primers are easily available when one requests DNA synthesis accession organization (e.g. QIAGEN). Thereupon, it is desirable to add a KOZAK sequence (Kozak M, J. Mol. Biol., 196, 947 (1987)) and a sequence of a suitable restriction enzyme cleavage site to 5' side. Preferably, synthetic DNAs described in SEQ ID NOs: 1 to 6, 13 and 15 are used as a primer. A PCR reaction may be performed using a commercially available Advantage HF-2 PCR Kit (BD Bioscience) according to an attached protocol. A nucleotide sequence of a DNA fragment obtained by PCR is cloned using a TA cloning kit (Invitrogen) and the like, and is sequenced with a DNA sequencer such as ABI PRISM310 Genetic Analyzer (PE Biosystems).

Using the thus obtained fibrinogen gene, preferably, a gene fragment having a sequence described in SEQ ID NO: 7 to 9, 14 or 16, an expression vector for incorporating into an animal cell is constructed. An expression vector for a host of an animal cell is not particularly limited, but a plasmid, a virus vector and the like can be used. A promoter contained in the expression vector may be any promoter such as a SV40 early promoter, a SV40 late promoter, a cytomegalovirus promoter, and a chicken actin promoter depending on a combination with an animal cell to be used as a host, as far as assembled fibrinogen is finally obtained. Preferably, a chicken β-actin promoter system expression plasmid pCAGG (JP-A No. 3-168087) is used. As a marker gene for selection or gene amplification, the generally known marker gene for selection or gene amplification such as an aminoglycoside 3' phosphotransferase (neo) gene, a dihydrofolate reductase (dhfr) gene, a puromycin resistance enzyme gene, and a glutamine synthetase (GS) gene (authored by Kriegler M, translated under supervision by Ikunoshin Kato, Genetic Engineering of Labo Manual Animal Cell, TAKARASHUZO Co., Ltd. (1994)) can be utilized.

Preferable examples of an expression vector constructed by combining the aforementioned elements include an expression vector having a gene encoding a γ chain and a β chain, and an expression vector having a gene encoding a γ chain and an α chain. More preferably, examples include pCAGGD-GB (having each one of gene encoding fibrinogen γ chain or β chain, and having a dhfr gene as a selectable marker) and pCAGGDN5-GA (having each one of a gene encoding fibrinogen γ chain or α chain, and having a dhfr gene and a neo gene as a selectable marker) shown in FIG. 1. These two kinds of expression vectors are mixed at an equal amount so that a constitutional ratio of a γ chain gene relative to an α chain an β chain gene becomes an equal amount, and introduced into an animal cell. However, the present invention is not limited to this example. The most important point of the present invention is to incorporate at a constitutional ratio of respective genes encoding three kinds of polypeptides, an α chain, a β chain and a γ chain, constituting fibrinogen finally introduced into a host cell in a host cell so that the number of a γ chain (and/or variant of γ chain) gene becomes an equal amount or more relative to a total number of an α chain (and/or variant of a chain) gene and a β chain gene. Herein, "incorporate" in the present invention includes not only a step of introducing a gene into a cell, but also a step of gene-amplifying an introduced gene by any method, and the state where a gene is finally integrated into a host cell genome. A constitutional ratio of genes can be regulated in a step of introducing a gene or a step of amplifying a gene introduced into a genome. For example, when a dhfr gene is used to perform gene amplification using a drug such as methotrexate, the number of an objective gene can e amplified to from a few copies to 2000 copies in a genome (Iman A M et al., J Biol. Chem., 262, 7368 (1987); Lau Y F et al., Mol Cell Biol., 4, 1469, 1984; Crouse G F et al., Mol Cell Biol., 3, 257, 1983. This shows when a dhfr gene is γ chain gene-selectively added, this is introduced into a host cell genome, and gene amplification is performed using a drug such as methotrexate, the number of a gene can be increased to from a few copies to 2000 copies γ chain gene-specifically, and shows that it is technically possible to realize a constitutional ratio of 1-fold to 1000-fold relative to a total number of an α chain β chain gene. Therefore, it is possible to adjust a constitutional ratio of incorporated genes such that the number of a γ chain (and/or variant of γ chain) gene is an equal amount to 1000-fold relative to a total number of an α chain (and/or variant of α chain) gene and a β chain gene.

In addition, also in a step of introducing a gene, when an animal cell is transformed using genes encoding an α chain, a β chain and a γ chain, transformation may be performed by adjusting a constitutional ratio of the genes to be introduced so that a γ chain becomes at least an equal amount to a 1000-fold amount as compared with a gene encoding other two α chain and β chain. Inter alia, a most preferable ratio includes an equal amount to a 3-fold amount. In the case of a method satisfying these requirements, it is not necessary that genes encoding respective chains are present in one expression vector as described above and, for example, as described above, an expression vector having each one of an α chain and a β chain, and an expression vector having two γ chains are mixed at an equal amount to a constitutional ratio of 1:1:2, and this may be introduced into an animal cell. Alternatively, expression vectors constructed so that an α chain, a β chain and a γ chain are expressed alone are mixed at a ratio of 1:1:2 to 6, and an animal cell may be transformed with the mixture. Alternatively, an animal cell may be transformed using an expression vector constructed so that a constitutional ratio of respective genes of an α chain, a β chain and a γ chain becomes 1:1:2 to 6 in one expression vector. Further, such a ratio that the number of a γ chain (and/or variant of γ chain) gene is an equal amount to a 3-fold amount relative to a total number of an α chain (and/or variant of α chain) gene and a β chain gene, such as 1:2:3 to 9, 1:3:4 to 12, and 2:3:5 to 15 (or 2:1:3 to 9, 3:1:4 to 12, 3:2:5 to 15) in addition to the aforementioned ratio of 1:1:2 to 6 satisfies the requirement of the present invention. Alternatively, in place of introducing all genes into an animal cell simultaneously, genes may be successively introduced into an animal cell at different times by changing a selectable marker, so that a constitutional ratio of respective genes of an α chain, a β chain and a γ chain to be finally introduced into a cell becomes the aforementioned ratio (equal-fold to 1000-fold). Alternatively, even when a ratio is not the aforementioned ratio at an introduction step as described above, a selectable marker which enables gene amplification such as a dhfr gene and a GS gene may be added to an expression vector having a γ chain gene, and gene amplification may be performed to realize the aforementioned ratio (equal-fold to 1000-fold) in a cell.

As a production amount potentiating factor, a factor having the action of increasing protein biosynthesis activity and/or the action of inhibiting caspase can be used, and representative examples include a P35 gene of baculovirus (AcNPV or BmNPV). For example, a baculovirus (AcNPV) P35 gene can be obtained by designing PCR primers based on the sequence reported in the literature (Friesen, P. D. and Miller, L. K., J. Virol. 61:2264-2272 (1987)), and performing PCR using a baculovirus-infected cell or virus genome itself as a template. Preferably, synthetic DNAs described in SEQ ID NOs: 10 and 11 are used as a primer. A PCR reaction may be performed using a commercially available Advantage HF-2 PCR Kit (BD Bioscience) according to an attached protocol. A nucleotide sequence of a DNA fragment obtained by PCR is cloned using a TA cloning kit (Invitrogen) and the like, and is then sequenced with a DNA sequencer such as ABI PRISM310 Genetic Analyzer (PE Biosystems). Using the thus obtained P35 gene, preferably, a gene fragment having a sequence described in SEQ ID NO: 12, an expression vector for incorporation into an animal cell is constructed. Preferable examples include vectors shown in FIG. 3. These are introduced into an animal cell, but the present invention is not limited to these examples. There is no particular limitation as far as it is such a form that a gene encoding a factor having production amount potentiating action, a representative of which is a baculovirus P35 gene, and an objective production gene, a representative of which is three kinds of genes of an α chain, a β chain and a γ chain constituting fibrinogen can be expressed simultaneously in the same cell. An introduction time and an introduction order of an expression vector for a gene encoding a baculovirus P35 gene, and an expression vector for three kinds of genes of an α chain, a β chain and a γ chain constituting fibrinogen are also not particularly limited. For example, an expression vector for a gene encoding a factor having production amount potentiating action, and a fibrinogen expressing vector may be introduced into a host cell simultaneously, or may be introduced at different times. When an expression vector for a gene encoding a factor having production amount potentiating action is introduced into a host cell in advance to produce a new host cell, versatility is further increased. However, when an expression vector having a gene encoding a factor having production amount potentiating action and an expression vector having a fibrinogen gene are introduced into a host cell at different times, it is necessary to use different selectable marker genes possessed by respective expression vectors.

As a host cell into which an expression vector is introduced, various animal cells such as a Chinese hamster ovary (CHO) cell, a mouse myeloma cell such as SP2/0, a BHK cell, a 293 cell, and a COS cell can be utilized, and a suitable cell may be selected in conformity with a promoter used in an expression vector, and a marker gene for selection and gene amplification. For example, in an expression vector constructed using a chicken β-actin promoter system expression plasmid, a BHK21 cell, a CHO cell DG44 strain and the like are used.

At transformation of a host cell, the known method may be utilized. For example, a calcium phosphate method, a DEAE dextran method, a method using a lipofectin-based liposome, a protoplast polyethylene glycol fusing method, and an electroporation method can be utilized, and a suitable method may be selected depending on a host cell to be used (Molecular Cloning ($3^{rd}$ Ed.), Vol. 3, Cold Spring Harbor Laboratory Press (2001)).

For selecting and proliferating a transformed cell, generally, a method which is performed at transformation of an animal cell may be used. For example, a cell after transformation is cultured at around 37° C. for about 10 to 14 days while a medium is conveniently exchanged, using a selective medium obtained by adding methotrexate, G418, puromycin and the like to a medium which is generally used in culturing an animal cell such as a serum-free medium such as a CHO-S-SFMII medium (GIBCO-BRL), an IS CHO-V medium (IS Japan), a YMM medium and the like, and a serum medium in which around 5 to 10% bovine fetal serum is added to a MEM alpha medium, a RPMI medium, or a Dulbecco's MEM medium (all GIBCO-BRL), depending on a selectable marker to be used. By this culturing, an untransformed cell dies, and only a transformed cell is grown. Further, for a transformed cell, an objective fibrinogen producing cell strain is selected and cloned by a method such as a limiting dilution method. In a culturing method, a method which is generally used in detecting a protein or a polypeptide, that is, a method such as ELISA, RIA, WB, SDS-PAGE and the like may be used for detecting fibrinogen or measuring an expression amount thereof, depending on a kind of a cell. Alternatively, clotting which is activity of fibrinogen may be directly measured.

The thus obtained present recombinant fibrinogen producing cell is a useful cell which expresses ~about 100 μg fibrinogen per 1 ml of a culturing solution by inoculating in a serum-containing medium at about $5 \times 10^4$ cells/ml and culturing this for 4 days, can be proliferated also in a serum-free medium without decreasing this fibrinogen production amount, and can attain ~about 270 μg production amount (potential production amount ~1520 μg/ml) per 1 ml of a culturing solution by seeding at about $1.6 \times 10^5$/ml and spinner-culturing this for about 2 weeks. In addition, although a production amount of fibrinogen by the prior art was a maximum of about 15 μg/ml, but when a P35 gene was introduced according to the present invention, about 42-fold production amount potentiating effect was resulted at a spinner culturing level. In addition, when a P35 gene is introduced, it is presumed that a potential production amount of about 704 to 3952 μg/ml is possessed as simply calculated.

The previous production potentiating effect due to apoptosis suppressing activity was thought that the effect is manifested maximally in culturing under the condition for inducing apoptosis in a protein producing cell such as mixing culturing with a drug exhibiting expression potentiating activity at a concentration region showing cytotoxicity at a later stage of culturing where nutrient condition is deteriorated, such as butyric acid, or any factor exhibiting cytotoxicity. The present invention exerts the effect in culturing not under such the special condition, but under the general culturing condition, that is, at a term where a normal survival rate is not reduced. This point is clearly different from the previous production amount potentiation due to apoptosis suppressing factor. Since the present invention can be used together with a rearing method such as fed batch culturing, and perfusion culturing, the fibrinogen producing ability of a recombinant cell can be further potentiated. Therefore, the present invention enables industrialization of fibrinogen production which has previously been difficult to produce, and difficult to be industrialized in an animal cell, and considerable cost down due to further production amount potentiation also in fibrinogen production which has already industrialized.

The present invention will be explained further specifically below by way of Examples, but the present invention is not limited to them. In the following Examples, unless indicated otherwise, reagents manufactured by Wako Pure Chemical Industries, Ltd., TAKARA SHUZOU Co., Ltd., Toyobo Co., Ltd., New England BioLabs, Amersham Pharmacia, BioLab, Sigma, and Gibco BRL were used.

Example 1

Isolation of Fibrinogen Gene

For a human fibrinogen gene, as a primer, each two primers consisting of a Kozak sequence and an added necessary enzyme site for an α chain, a β chain, and a γ chain were prepared (SEQ ID NOs: 1 to 6), and a PCR reaction was performed using Advantage HF-2 PCR Kit (BD Bioscience) and employing Human Liver Marathon-Ready cDNA (BD Bioscience) as a template according to a protocol of the kit. As a result, a band of PCR amplification was detected in each of an α chain, a β chain, and a γ chain. Since its size was coincident with each size of the known α chain, β chain, and γ chain, cDNA genes, these genes were cloned (pFbgA, pFbgB, pFbgG, respectively) using a TA cloning kit (Invitrogen), and its nucleotide sequence was determined using ABI PRISM310 Genetic Analyzer (PE Biosystems). As a result, FbgA, FbgB and FbgG genes shown in SEQ ID NOs: 7 to 9, respectively, were obtained.

Example 2

Construction of Fibrinogen Gene Expression Vector

A fibrinogen β chain and γ chain gene expression vector pCAGGD-GB, and a fibrinogen α chain and γ chain gene expression vector pCAGGDN5-GA used in the present Example were constructed as follows: For pCAGGD-GB, first, pCAGG-S1 dhfr (WO 03/004641) was digested with BamHI, blunt-ended with a T4 DNA polymerase, and ligated using a phosphorylation NotI linker (TAKARA SHUZOU Co., Ltd.) to construct pCAGG-S1 dhfrN, and into the SalI site thereof was incorporated a SalI fragment of a FbgG gene derived from pFbgG to construct pCAGGD-G. Further, pCAGG(Xho) (WO 03/004641) was digested with SalI, blunt-ended with a T4 DNA polymerase, and ligated using a phosphorylation NotI linker (TAKARA SHUZOU CO., Ltd.) to construct pCAGG (Xho) N, a XbaI-BamHI fragment containing SalI of pCAGG-S1 (WO 03/004641) was incorporated into a XbaI-BamHI site of this plasmid, a BamHI site of the resulting plasmid was digested, blunt-ended with a T4 DNA polymerase, and ligated using a phosphorylation NotI linker (TAKARA SHUZOU Co., Ltd.) to construct pCAGG-S1 2N. A SalI fragment of a FbgB gene derived from pFbgB was incorporated into a SalI site of this pCAGG-S1 2N to construct pCAGG-B. A NotI fragment containing a FbgB gene of pCAGG-B was incorporated into a NotI site of pCAGGD-G, to construct a final fibrinogenβ chain and γ chain expression vector pCAGGD-GB (FIG. 1).

On the other hand, pCAGGDN5-GA, initially, pCAGG-S1 dhfr neo (WO 03/004641) was incompletely digested with BamHI, blunt-ended with a T4 DNA polymerase, this was as it was self-ligated to delete a BamHI site 3'-position of a neo gene among two BamHI sites, this was further digested with BamHI, blunt-ended with a T4 DNA polymerase, and ligated using a phosphorylation NotI linker (TAKARA SHUZOU Co., Ltd.) to construct pCAGG-S1 dhfr neoN (pCAGGDN5-NotI). A SalI fragment containing a FbgG gene derived from pFbgG was inserted into a SalI site of this pCAGG-S1 dhfr neoN to construct a plasmid, into a NotI site of the plasmid was incorporated into a NotI fragment containing a FbgA gene of pCAGG-A constructed by inserting a SalI fragment containing a FbgA gene derived from pFbgA into a SalI site of pCAGG-S1 2N, to construct pCAGGDN5-GA (FIG. 1).

Example 3

Preparation of Recombinant Fibrinogen Expressing Cell: Introduction of Expression Vector into Cell, Gene Amplification, Cloning Using fibrinogen expression plasmids pCAGGD-GB and pCAGGDN5-GA constructed in Example 2, a CHO DG44 (Urlaub G et al., Somatic cells. Mol. Genet., 12, 555 (1986), hereinafter, CHO) cell was transformed by the following method. On a day before transformation, a CHO cell was seeded on a 6 well plate at a cell density of 1 to $0.5 \times 10^5$ cells/2 ml/well using a YMM medium (nucleic acid-free MEM alpha medium enriched in amino acid and vitamin containing insulin, transferrin, ethanolamine and sodium selenite) containing 10% bovine fetal serum (FCS, manufactured by GIBCO-BRL). After culturing at 37° C. with a 5% $CO_2$ culturing device overnight, transfection was performed according to each protocol using an introduction DNA obtained by mixing each equal amount of fibrinogen expression plasmids pCAGGD-GB and pCAGGDN5-GA, and digesting and linearizing the mixture with PvuI in advance, and using a liposome transformation reagent, TransIT-LT1 (TAKARA SHUZOU Co., Ltd.) or lipofectamine 2000 (Invitrogen). After culturing at 37° C. with a 5% $CO_2$ culturing device overnight, a medium was exchanged with a selective medium, a YMM medium containing 10% dialysis FCS (d-FCS: manufactured by GIBCO-BRL), 0.5 mg/ml Geneticin (manufactured by G418: GIBCO-BRL), and 100 nM methotrexate (MTX: manufactured by Wako Pure Chemical Industries, Ltd.), or a YMM medium containing 10% d-FCS, and 0.5 mg/ml G418. Selection was performed by continuing culturing at 37° C. with a 5% $CO_2$ culturing device while a medium was exchanged every 3 or 4 day to obtain a transformant.

Fibrinogen production by the resulting transformed cell was measured by ELISA. ELISA was performed by the following procedure. 100 μl of an anti-human fibrinogen rabbit polyclonal antibody (Dako Cytomation) which had been adjusted with PBS (137 mM NaCl, 8 mM $Na_2HPO_4$-$12H_2O$, 2.7 mM KCl, 1.5 mM $KH_2PO_4$) to 10 μg/ml was applied to an immunomodule plate (Nunc C8-445101), and this was allowed to stand at 4° C. overnight to perform solid phasing. An antibody solution of a solid phased plate was removed, and washed with 390 μl of PBS three times. Subsequently, 370 μl of Block Ace (Dainippon Pharmaceutical Co., Ltd.)

which had been diluted 4-fold with PBS was applied, and blocking was performed at room temperature for 30 minutes to 2 hours. After blocking, a blocking solution was removed, 100 μl of a sample (culturing supernatant) or a standard was applied. A sample (culturing supernatant of fibrinogen producing cell) was diluted 100 to 800-fold using Block Ace which had been diluted 10-fold with PBS. As a standard, Bolheal (manufactured by Kaketsuken: vial 1 containing fibrinogen derived from plasma was dissolved according to the specification, and diluted with PBS to 1 mg/ml by calculation using its fibrinogen amount as 80 mg/ml) which had been diluted to 100 ng/ml to ing/ml with the same diluent as that of a sample, was used. A sample and a standard were applied to a plate, followed by a reaction at 37° C. for 1 hour. After completion of the reaction, the reaction was washed with 390 μl of a detergent (0.05% Tween-20/PBS) four times, subsequently, 100 μl of an anti-human fibrinogen rabbit polyclonal antibody raveled with peroxidase which had been diluted 8000-fold with a solution (Block Ace diluted 10-fold with PBS) used in diluting a sample was applied, followed by the reaction at 37° C. for 1 hour. After completion of the reaction, the reaction was washed with 390 μl of a detergent (0.05% Tween-20/PBS) four times. Development was performed by applying 100 μl of TMB Substrate Kit (Kirkegaard & Perry Laboratories, Inc.), this was allowed to stand in a dark place for 30 minutes, and the reaction was stopped with 100 μl of 1N sulfuric acid. Within 30 minutes after stoppage of the reaction, an absorbance at 450 nm to 650 nm was measured with a plate reader (molecular device), and a fibrinogen concentration was obtained from a calibration curve.

By this ELISA, a transformed cell having the high fibrinogen producing ability was selected and, then, amplification of a MTX gene was performed. A cell was suspended in a YMM medium containing 10% d-FCS, and 0.5 mg/ml G418 and having an step wisely increased MTX concentration, this was seeded on a 24 well plate at $5 \times 10^4$ cells/0.5 ml/well, and selection was performed by continuing culturing at 37° C. with a 5% $CO_2$ culturing device while a medium was exchanged every 3 to 4 day, to obtain a transformant which is resistant to highly concentrated MTX. Table 1 shows representative results ("*" in Table: a medium was completely exchanged with a fresh medium at confluence of a cell, and the cell was cultured overnight; production amount in the culturing supernatant at that time).

TABLE 1

| Cell name | MTX concentration (μM) | Production amount (μg/ml) * |
|---|---|---|
| CH002-24 | 0.1 | 24.4 |
| CH003-1A4 | 3 | 20.3 |
| CH004-2A4 | 0.5 | 32 |
| CH004-2A5 | 0.5 | 36 |
| CH004-13A7B2 | 3 | 28 |
| CH006-3A1 | 4 | 45.3 |
| CH006-13 | 24 | 34 |
| CH006-19A1 | 4 | 33 |

Such the recombinant fibrinogen producing cell was cloned. A cell was suspended in a YMM medium containing 10% d-FCS, 0.5 mg/ml G418, and 100 nM MTX, and each 200 μl/well of the suspension was seeded on a 96 well plate at a concentration of 1/well, thereby, cloning by limiting dilution was performed. A medium was completely exchanged with a fresh medium at confluence, the resulting clone was cultured overnight, and a production amount in the culturing supernatant was investigated, and clones reaching up to 56.8 μg/ml were obtained. Among them, a cell of one clone CH002-24-4 was suspended in a YMM medium containing 10% d-FCS, 0.5 mg/ml G418, and 100 nM MTX, the suspension was seeded on a 6-well plate at $2 \times 10^5$ cells/2 ml/well, this was cultured for 4 days, an amount of fibrinogen in the culturing supernatant was measured by an ELISA method, the amount was found to reach 103.3 μg/ml, and it was shown that an amount as a production amount of fibrinogen by a recombinant animal cell first exceeded a 100 μg/ml order.

Example 4

Western Blot Analysis of Produced Fibrinogen

Western blotting of produced fibrinogen was performed. As a fibrinogen sample, a CH001-1-2 cell was seeded at a density of $2 \times 10^5$ cells/ml using a YMM medium containing 10% d-FCS, this was cultured overnight and, on a next day, a medium was exchanged with a YMM medium containing no FCS, this was cultured at 37° C. for 4 days with a 5% $CO_2$ culturing device, and fibrinogen present in the culturing supernatant was used for analysis.

The sample was mixed with a 5×SDS-treated buffer (0.3125M Tris, 5% SDS, 25% glycerol, 0.05% bromophenol blue, 5% 2-mercaptoethanol pH6.8) 1:4, and this was boiled at 100° C. for 5 minutes. These samples were electrophoresed for 1.5 hours under the electrophoresing condition of 40 mA constant current using Pagel 5 to 20% (ATTO) as a gel. After electrophoresis, a gel and Immobilon Transfer Membranes (hereinafter, Membrane: MILLIPORE) were adhered, and the electrophoresed protein was transferred to Membrane at 100 mA constant current for 25 minutes using Holize blot (ATTO). A Membrane was blocked with a Block Ace (Dainippon Pharmaceutical Co., Ltd.) stock solution at room temperature for 1 hour and, then, immersed in 10% Block Ace, 0.05% Tween-20/TBS (50 mM Tris, 150 mM NaCl pH7.5) containing 0.55 μg/ml of an anti-human fibrinogen rabbit polyclonal antibody (Dako Cytomation), followed by shaking at 37° C. for 30 minutes. Further, shaking with 0.05% Tween-20/TBS for 5 minutes was repeated three times to wash, and this was washed with TBS three times, and blocked with a Block Ace (Dainippon Pharmaceutical Co., Ltd.) stock solution at room temperature for 5 minutes. Subsequently, this was immersed in a Goat Anti-Rabbit IgG-Alkaline Phosphatase Conjugate (BIOSOURCE) solution which had been diluted 3000-fold with 10% Block Ace, 0.05% Tween-20/TBS, followed by shaking at 37° C. for 30 minutes. Shaking with 0.05%, Tween-20/TBS for 5 minutes was repeated three times to wash, and this was further washed with TBS three times, and developed with Phosphatase Substrate (KPL).

Figure 2:
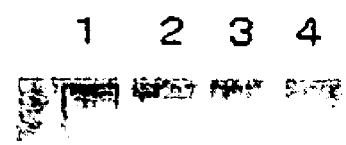
FIG. 2 is a view showing the result of a Western blotting profile of produced fibrinogen. lane 1: marker (Amersham Rainbow Marker 756), lane 2: Bolheal (manufactured by Kaketsuken: A vial 1 containing plasma-derived fibrinogen was dissolved according to the provision, the fibrinogen amount was calculated as 80 mg/ml, and this was diluted with PBS. 1 μg/lane), lane 3: CH001-1-2 culture supernatant (8 μl/lane), lane 4: CH001-1-2 culture supernatant (24 μl/lane).
Figure 2:
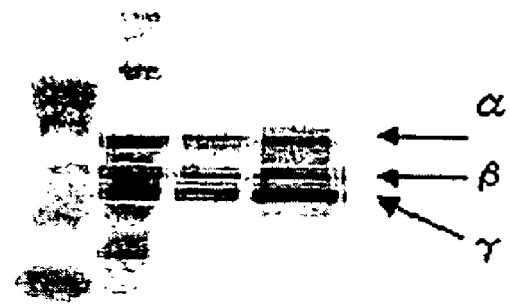

Results thereof are shown in FIG. 2. It was confirmed that, under reduction, fibrinogen produced in the CH001-1-2 culturing supernatant contains a protein having the same size as that of borhyl containing fibrinogen derived from plasma. In addition, these three bands were coincident with molecular weighs of the known respective fibrinogen chains: α chain; 66 kDa, β chain; 52 kDa, γ chain; 46.5 kDa.

Example 5

Serum-Free Culturing of Recombinant Fibrinogen Producing Cell

The producing ability of a recombinant fibrinogen producing cell was investigated at self-free culturing. The clone CH002-24-4 exhibiting a production amount of 100 μg/ml or more in Example 3 was washed with PBS two times, suspended in a medium shown in Table 2 (serum-free medium for CHO-S-SFMII, IS CHO-V, and serum medium for 10% d-FCS/YMM), 2 ml/well of 6 well plate of the suspension was seeded at $10^5$ cells/ml, this was cultured for 4 days, and a count of the resulting cell number, and a fibrinogen production amount in the culturing supernatant were measured by the aforementioned ELISA. As a result, as shown in Table 2, the fibrinogen producing ability per $1\times10^4$ cells was higher than the case where a serum medium (YMM medium containing 10% d-FCS) was used, and it was shown that there is the equal or more producing ability to that of a serum medium also in a serum-free medium. This shows that since 1 to $2\times10^6$ cells/ml can be attained at general high density culturing, even if the culturing condition is better, there is the potential ability of producing about 440 to 1520 μg/ml or more of fibrinogen by simple calculation.

TABLE 2

| Medium | Maker | Production amount (μg/1 × $10^4$cells) |
| --- | --- | --- |
| 10% d-FCS/YMM | Self preparation | 2.0 |
| CHO-S-SFMII | GIBCO | 4.4 |
| IS CHO-V | IS Japan | 7.6 |

Further, the CH002-24-4 cell which had been grown on this CHO-S-SFMII medium was seeded on 100 ml of a serum-free medium similarly containing mainly CHO-S-SFMII at $1.6\times10^5$ cells/ml, and 272.7 μg/ml of a production amount was attained by suspension culturing (rotation number 45 rpm) for about 2 weeks using a spinner-flask manufactured by TECHNE. Separately, another clone CH004-2A4-3 cell was seeded on 100 ml of a serum-free medium similarly containing mainly CHO-S-SFMII at $8\times10^4$ cells/ml, and 98.2 μg/ml was attained by suspension culturing (rotation number 45 rpm) for about 2 weeks using a spinner flask manufactured by TECHNE. Like this, the cell established by the method of the present invention attained up to about 270 μg/ml of a production amount on a serum-free medium regarding fibrinogen production, and it was shown that the cell is a highly productive cell which has not previously been obtained.

Example 6

Cloning of P35 Gene and Construction of Expression Vector

A virus genome was prepared from a baculovirus AcNPV (Autographa california nuclear polyhedrosis virus: purchased from Invitrogen)-derived virus solution ($2\times10^7$ pf/ml) by protenase K treatment and phenol extraction, this was used as a template and, two primers, 5' primer and 3' primer, consisting of a Kozak sequence and a necessarily added enzyme site were prepared (SEQ ID NOs: 10 and 11), and a PCR reaction was performed using Advantage HF-2 PCR Kit (BD Bioscience). Since a size of the PCR product was coincident with a size of the known P35 gene, this was subjected to TA cloning (Invitrogen). Regarding the resulting plasmid, its nucleotide sequence was determined using ABI PRISM310 Genetic analyzer (PE Biosystems) and, as a result, a P35 gene clone (SEQ ID NO:12) having the same sequence as the sequence of the publication (Friesen P D, Miller L K, J Virol. 61(7): 2264-72.1987) was obtained.

Figure 3:
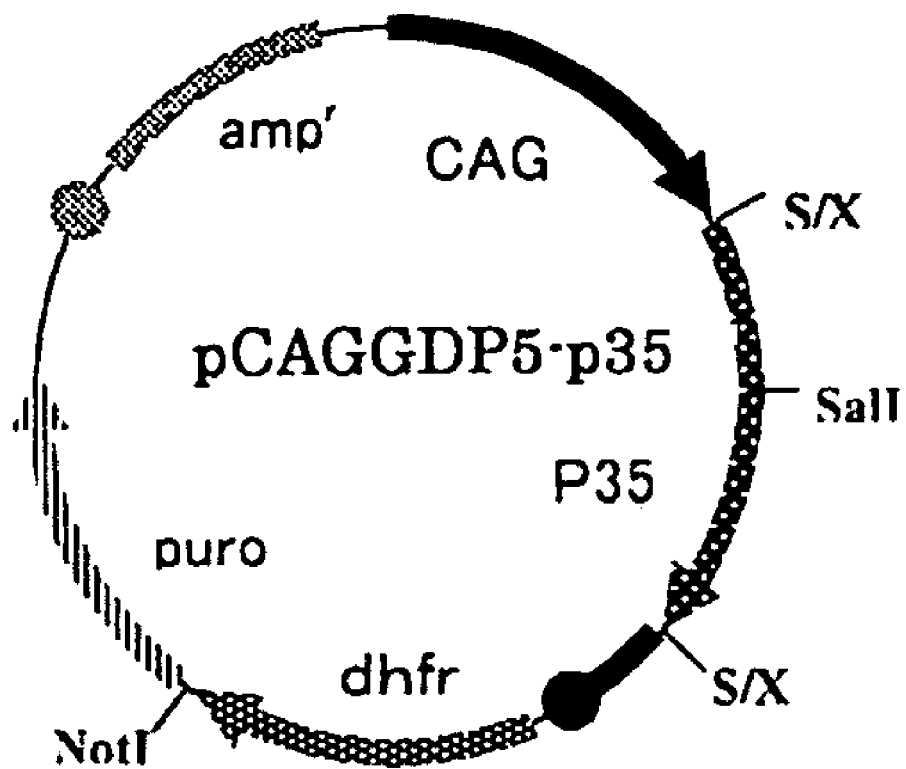
FIG. 3 is a view showing an expression vector for producing a baculovirus P35 gene expressing cell.

In order to introduce a P35 gene into a cell which had already been expressing fibrinogen, first, a vector having a puromycin resistant gene as a selectable marker was constructed. In order to insert a BamHI site between SapI and NotI site of an expression plasmid pCAGG-S1 mdhfr (WO 03/004641) having mutated DHFR in which $23^{rd}$ serine was converted into arginine, two linkers of GGC CGC GGA TCC GCT CTT CC and AGC GGA AGA GCG GAT CCG C were synthesized, and ligated with a linker to construct pCAGGM5. Further, pCAGGM5 was digested with BamHI, blunt-ended with a T4 DNA polymerase, and linker-ligated using a XhoI linker (TAKARA SHUZOU Co., Ltd.) to introduce XhoI. A SalI fragment containing a puromycin resistance gene of pPGKPuro (Watanabe, S., Kai, N., Yasuda, M., Kohmura, N., Sanbo, M., Mishina, M., and Yagi, T. (1995)) was inserted into a XhoI site of this plasmid to construct pCAGGMP5-NotI. Then, a SalI-NotI fragment containing a mutated DHFR (mdhfr) gene was removed from this plasmid and, instead, a SalI-NotI fragment containing a DHFR gene of pCAGGDN5-NotI was inserted to construct pCAGGDP5-NotI. A XhoI fragment of a PCR-cloned P35 gene was inserted into a SalI site of pCAGGDP5-NotI to construct objective pCAGGDP5-P35 (FIG. 3).

Example 7

P35 Gene-Transformed Cell

A recombinant fibrinogen producing clone, a CH002-24-4 cell obtained in Example 3, was transformed using a P35 expression plasmid pCAGGDP5-P35 constructed in Example 6 by the following method. The CH002-24-4 cell was seeded on a 12 well plate at a cell density of 1 to $0.5\times10^5$ cells/ml/well using a CHO-S-SFMII medium (GIBCO-BRL). Using an introduction DNA obtained by digesting and linearizng the P35 expression plasmid pCAGGDP5-P35 with PvuI in advance using lipofectamine 2000 (Invitrogen) which is a liposome-based transforming regent, transfection was performed according to a protocol of lipofectamine 2000. After culturing at 37° C. with a 5% $CO_2$ culturing device overnight, a medium was exchanged with a CHO-S-SFMII medium containing 4 μg/mlpuromycin (BD Bioscience) as a selective medium. Selection was performed by continuing culturing at 37° C. with a 5% $CO_2$ culturing device while a medium was exchanged every 3 to 4 day, to obtain a transformant.

Figure 4:
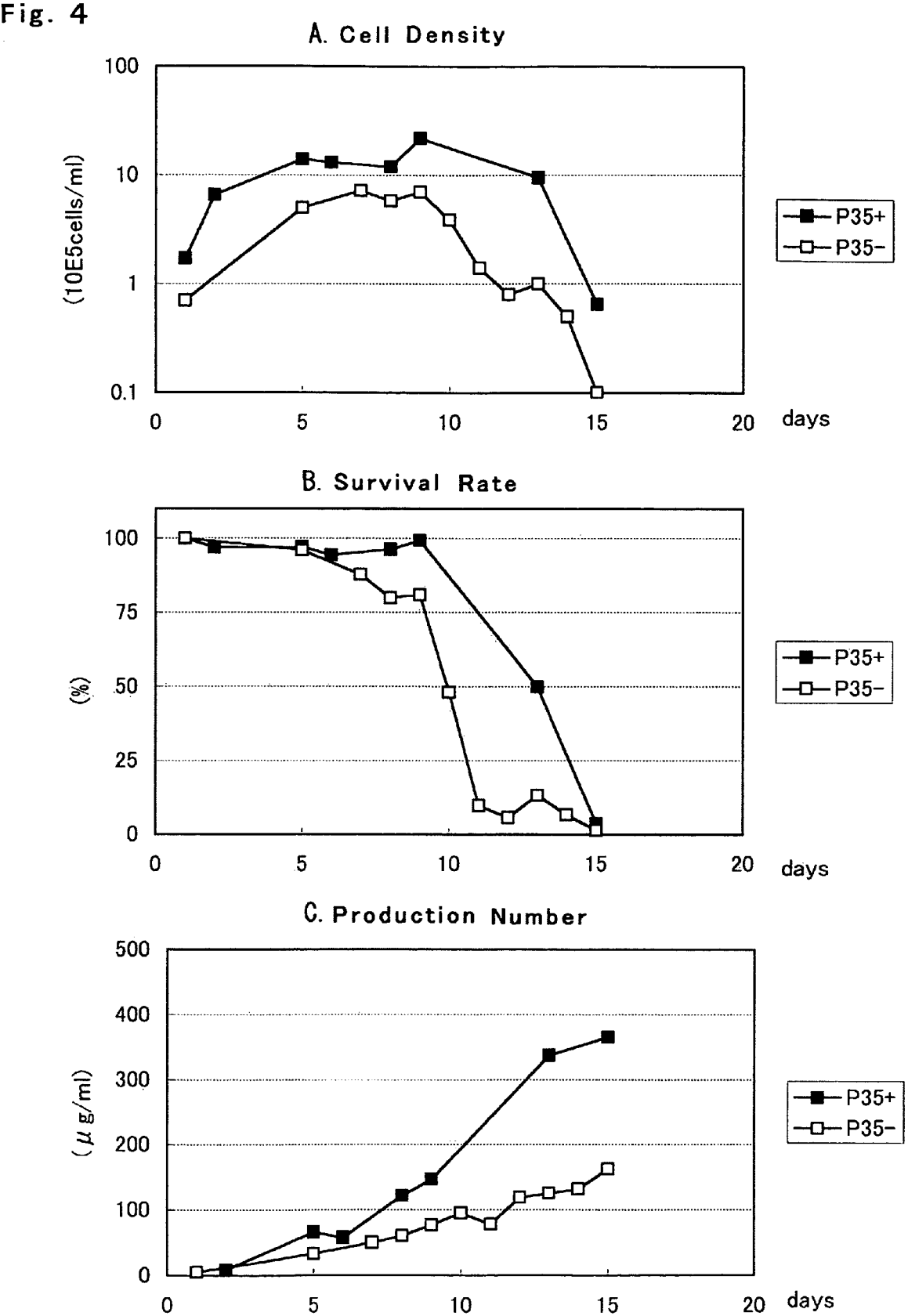
FIG. 4 is a view showing a change with time regarding a cell density, a survival rate, and a fibrinogen production amount in spinner culturing of a cell expressing a baculovirus P35 gene and a cell not expressing the gene.
Figure 5:
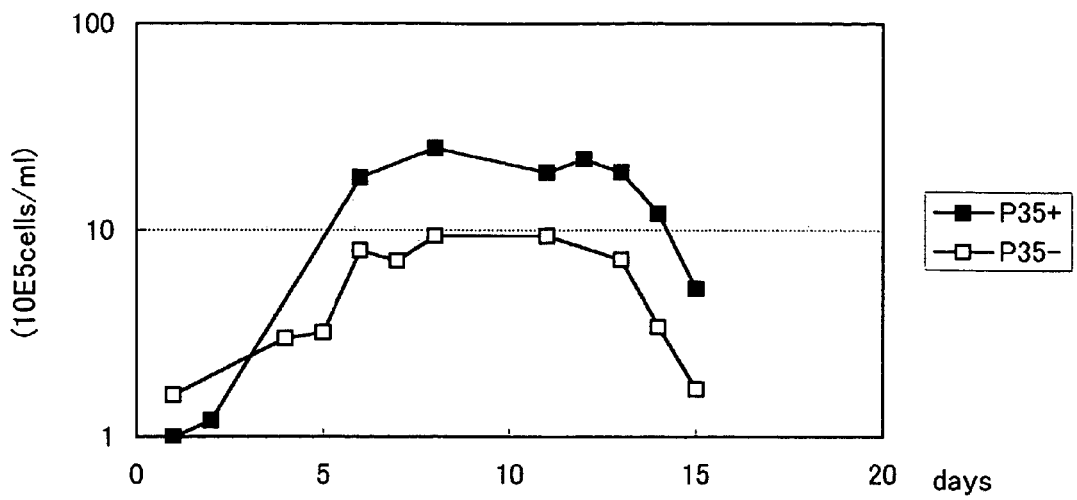
FIG. 5 is a view showing a change with time regarding a cell density, a survival rate, and a fibrinogen production amount in spinner culturing of a cell expressing a baculovirus P35 gene and a cell not expressing the gene.
Figure 5:
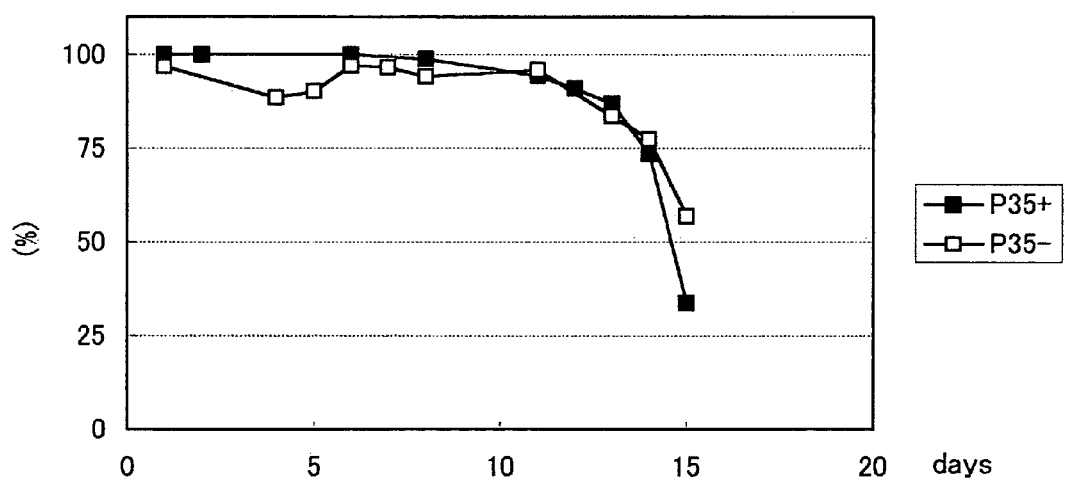
Figure 5:
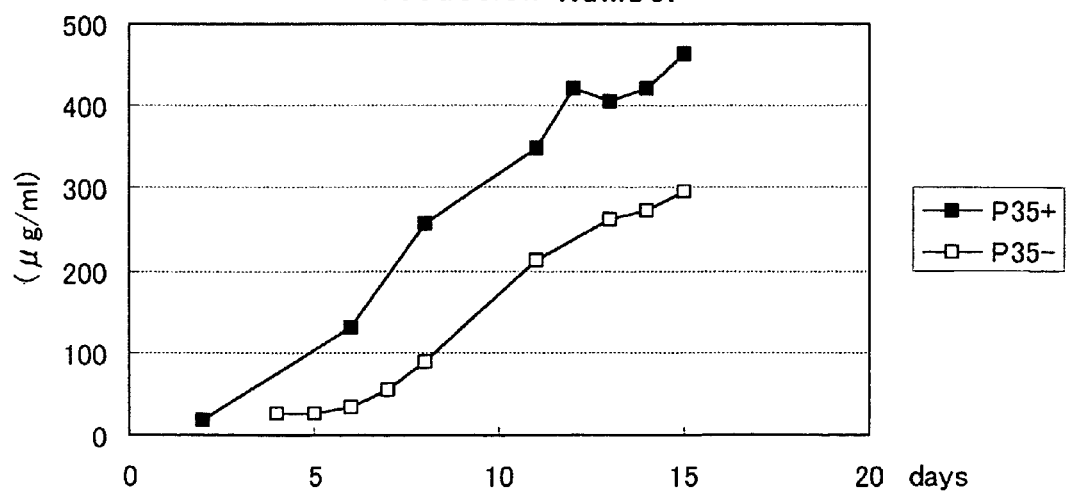

In order to investigate the effect of an introduced P35 gene, a P9 GD cell which is one of the resulting P35 gene transformants, and a 2-24-4 cell which is its parent strain were seeded on 100 ml of a CHO-S-SFMII medium at about $1.0\times10^5$ cells/ml, suspension culturing (rotation number 45 rpm) was performed for about 2 weeks using a spinner flask manufactured by Techne, and a growing curve, a survival rate, and a fibrinogen production amount were investigated. As a result, as shown in FIG. 4, a P9GD cell was increased to $2.2\times10^6$ cells/ml, and a 2-24-4 cell was increased to $7.2\times10^5$/cell ml by about 3-fold in terms of a maximum cell density. In addition, a P9GD cell reached a 50% survival rate later by 3 days as compared with a 2-24-4 cell. As a result, a production amount on 15 day of culturing increased to 365.2 μg/ml for a P9GD cell, and to 162.7 μg/ml for a 2-24-4 cell, by about 2.2-fold. Further, using a modified serum-free medium enriched in a nutrient component containing mainly a CHO-S-SFMII medium, spinner culturing was similarly performed, there was little difference in a survival rate as shown in FIG. 5, but a maximum cell density was increased to $9.4\times10^5$ cells/ml for a 2-24-4 cell by about 2.6-fold, as compared with $2.5\times10^6$ cell/ml for a P9 GD cell. Further, a production amount on 15 day of culturing was increased to 295.6 μg/ml for a 2-24-4 cell by about 1.6-fold as compared with 463.7 μg/ml for a P9GD cell.

Figure 6:
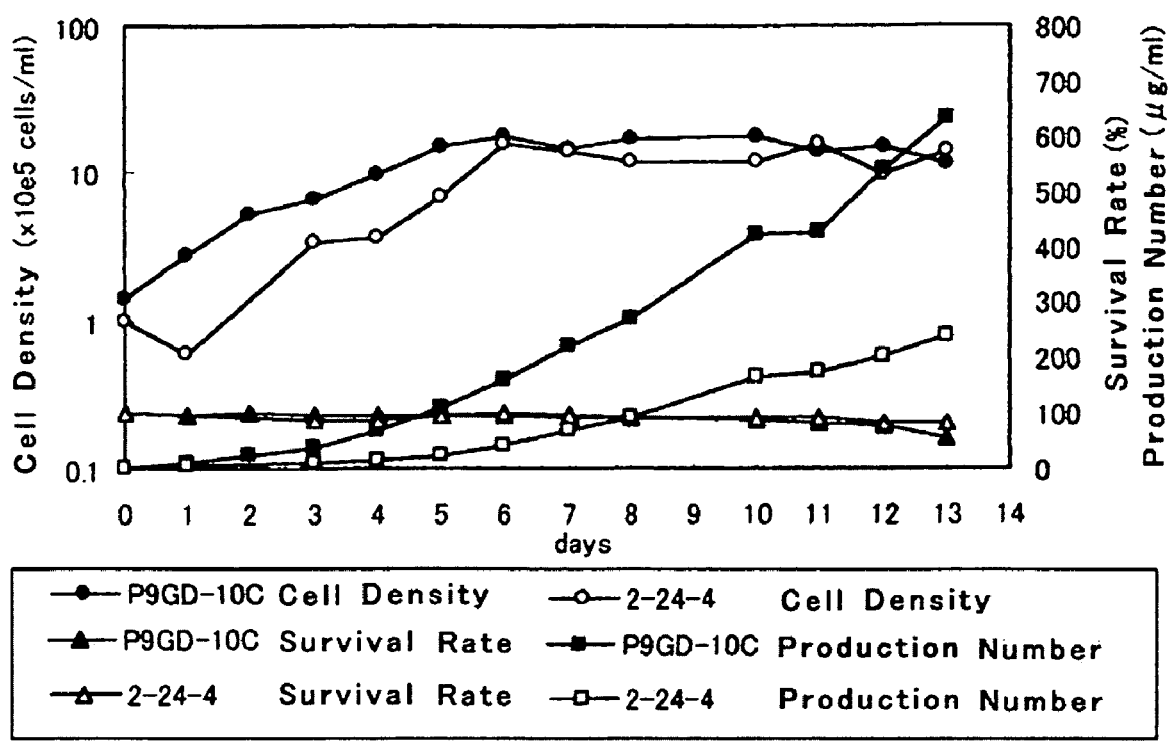
FIG. 6 is a view showing a change with time regarding a cell density, a survival rate, and a fibrinogen production amount in spinner culturing of a cell expressing a baculovirus P35 gene and a cell not expressing the gene.

A P9GD cell was cloned. A cell was suspended in a modified serum free medium containing mainly a CHO-S-SFMII medium, and this was seeded on a 96 well plate at 50/200 μl/well, thereby, cloning was performed. The resulting clone P9GD-10C was similarly spinner-cultured using a modified serum-free medium enriched in a nutrient component containing mainly a CHO-S-SFMII medium as in a P9GD cell, there was no difference in a survival rate and a reaching live cell density and, on 13 day of culturing, a production amount was increased to 631.5 μg/ml by about 2.6-fold relative to 239.8 μg/ml for a 2-24-4 cell (FIG. 6). Since there was not difference in a survival rate, and a live cell number, it was thought that a production amount was increased not by anti-apoptosis reaction of P35, but by protein biosynthesis active potentiating action possessed by P35.

As described in an item of Means to solve the problems, a maximum production amount of fibrinogen which had been known before the present invention was about 15 μg/ml and, in the case where a P35 gene was introduced by the present invention, the amount became 631.5 μg/ml at a spinner culturing level, and about 42-fold production amount potentiating effect was resulted. In addition, since the potential fibrinogen producing ability of a 2-24-4 cell which is a parent strain for P35 gene introduction is presumed to be 440 to 1520 μg/ml or more and, when a P35 gene is introduced, about 1.6 to 2.6-fold effect is seen, it is presumed that the potential production amount of about 704 to 3952 μg/ml is possessed as simply calculated. Like this, it was shown that a cell established by the method of the present invention is a cell which highly produces fibrinogen which had not been obtained.

Since a recombinant human fibrinogen producing cell obtained by the present invention highly produces fibrinogen, it can be utilized as an antigen upon preparation of monoclonal and polyclonal antibodies, or as a material for study regarding binding between an anti-human fibrinogen antibody and fibrinogen. Further, fibrinogen obtained by the present invention can be prepared by pure fibrinogen not containing a blood coagulation or fibrinolysis-associated factor other than fibrinogen, unlike fibrinogen derived from blood. Therefore, the cell is also useful as a material for study associated with blood coagulation and fibrinolysis. In addition, by using fibrinogen as an antigen alone, or together with various additives such as a stabilizer, a protecting agent and an antiseptic agent, it enables provision of a medicament such as an agent for arresting, preventing or treating morbid deterioration for various diseases. For example, the fibrinogen can be used for improvement in the consumption state of a blood coagulation factor such as DIC, and supplemental therapy in congenital and acquired fibrinogen deficiency.

In addition, the recombinant human fibrinogen of the present invention can be utilized as a tissue adhesive utilizing agglutination property of fibrin, for hemostasis, closure of a wound site, adhesive or suturing reinforcement of a nerve, a tendon, a vessel and a tissue, and therapy over a wide range such as closure of air leakage in lung, or as a suitable drug for a base of regeneration medicine for the purpose of tissue regeneration.

Like this, the recombinant fibrinogen producing cell obtained by the process of the present invention, and the recombinant human fibrinogen obtained by the cell greatly contribute in the medical and research field.

The invention claimed is:

1. A process for preparing a recombinant fibrinogen-producing cell which produces a high level of fibrinogen of 100 μg/ml or more, comprising transfecting, into an animal cell, genes encoding (i) an α chain and/or an αE variant thereof, (ii) a β chain, and (iii) a γ chain and/or a γ' variant thereof which are polypeptides constituting fibrinogen, wherein the number of genes encoding a γ chain and/or a γ' variant thereof is 1 to 3 times the sum of the number of genes encoding an α chain and/or an αE variant thereof and the number of genes encoding a β chain, wherein the animal cell transfected with the genes encoding the chains produces a high level of fibrinogen of 100 μg/ml or more.

2. The process according to claim 1, wherein the number of genes encoding a γ chain is the same as the sum of the number of genes encoding an α chain and the number of genes encoding a β chain.

3. The process according to claim 1 or 2, wherein an expression vector comprising a gene encoding an α chain and a gene encoding a γ chain, and an expression vector comprising a gene encoding a β chain and a gene encoding a γ chain are transfected into the animal cell either simultaneously or successively.

4. The process according to claim 3, wherein an expression vector comprising a gene encoding an α chain and a gene encoding a γ chain, and an expression vector comprising a gene encoding a β chain and a gene encoding a γ chain are transfected in equal amounts.

5. The process according to claim 1, wherein expression vectors pCAGGD-GB and pCAGGDN5-GA are mixed in equal amounts to form a mixture of expression vectors, and the mixture of expression vectors is transfected into the animal cell.

6. The process according to claim 1 or 2, wherein an expression vector comprising a gene encoding an α chain and a gene encoding a β chain, and an expression vector comprising a gene encoding a γ chain are ransfected into the animal cell either simultaneously or successively.

7. The process according to claim 1 or 2, wherein an expression vector comprising a gene encoding an α chain, an expression vector comprising a gene encoding a β chain and an expression vector comprising a gene encoding a γ chain are incorporated transfected into the animal cell either simultaneously or successively.

8. The process according to claim 1, wherein an expression vector comprising a promoter selected from the group consisting of a SV40 early promoter, a SV40 late promoter, a cytomegalovirus promoter and a chicken β-actin promoter, and a marker gene for gene amplification selected from the group consisting of an aminoglycoside 3' phosphotransferase (neo) gene, a puromycin resistance gene, a dihydrofolate reductase (dhfr) gene and a glutamine synthetase (GS) gene are used for transfecting the genes encoding the α-, β-, and γ-chains into the animal cell.

9. The process according to claim 8, wherein, in the expression vector, the promoter is a chicken β-actin promoter and the marker gene is a dihydrofolate reductase gene.

10. The process according to claim 1, wherein the animal cell is selected from the group consisting of a Chinese hamster ovary cell (CHO cell), a mouse myeloma cell, a baby hamster kidney (BHK) cell, a 293 cell and a COS cell.

11. The process according to claim 1, wherein the animal cell is a Chinese hamster ovary cell (CHO cell) of strain DG44.

12. The process according to claim 1, further comprising transfecting, into the animal cell, a baculovirus P35 gene at the same time as, or at a different time from, the genes encoding polypeptides constituting fibrinogen.

13. A recombinant fibrinogen producing cell obtained by the process of claim 2.

14. A process for producing fibrinogen, comprising culturing the recombinant animal cell obtained by the process of claim 12 under conditions in which cell apoptosis is not induced to produce fibrinogen in an amount of 100 μg/ml or more.

15. A process for producing fibrinogen, comprising culturing the recombinant animal cell of claim 13 by any of a fed batch culturing method, a perfusion culturing method, and a culturing method using a nutrient enriched medium to produce fibrinogen in an amount of 100 μg/ml or more.

16. A process for producing fibrinogen, comprising culturing the recombinant animal cell of claim 13 in a serum-free medium to produce fibrinogen in an amount of 100 μg/ml or more.

* * * * *